United States Patent [19]

DeCaprio et al.

[11] 4,243,033
[45] Jan. 6, 1981

[54] CATHETER DELIVERY SYSTEM

[75] Inventors: Vincent DeCaprio, Totowa; George Sanderson, Clark, both of N.J.

[73] Assignee: Becton, Dickinson and Company, Paramus, N.J.

[21] Appl. No.: 7,481

[22] Filed: Jan. 29, 1979

[51] Int. Cl.³ .............................................. A61M 5/00
[52] U.S. Cl. ................................ 128/214.4; 128/348; 128/DIG. 9
[58] Field of Search ................ 128/214.4, 348–351, 128/656–658, DIG. 9

[56] References Cited

U.S. PATENT DOCUMENTS

| | | | |
|---|---|---|---|
| 3,703,174 | 11/1972 | Smith | 128/214.4 |
| 3,826,256 | 7/1974 | Smith | 128/214.4 |
| 3,859,985 | 1/1975 | Eckhart | 128/274 X |
| 4,159,022 | 6/1979 | Pevsner | 128/214.4 |

*Primary Examiner*—Dalton L. Truluck
*Attorney, Agent, or Firm*—Kane, Dalsimer, Kane, Sullivan & Kurucz

[57] ABSTRACT

A method and apparatus for delivering a small elongated flexible member into a body cavity. The apparatus includes a storage chamber opened at both ends for containing substantially the entire length of the member to be delivered with one end extending through the opening at the forward end of the chamber and the other end extending through the opening at the rear end of the chamber. A first valve is attached to the rear end of the chamber and has a passageway therethrough in communication with the interior of the chamber so that extension of the other end of the member through the valve and closing of the valve will retain the other end of the member in fixed position. A fluid port is positioned between this valve and the chamber and has a passageway in communication with the interior of the chamber. A second fluid port is attached to the forward end of the chamber in position on a nozzle and has a passageway therethrough in communication with the interior of the chamber. A second valve is on the nozzle in position between the fluid port and the chamber to fix the one end of the member in position when extended through the nozzle from the chamber. The chamber and nozzle are fluid-filled. Fluid pressure from a liquid pressure source directs fluid through the fluid port and nozzle so that when the second valve means is opened the one end of the member and a portion in the chamber will be delivered through the forward end of the nozzle and from the apparatus.

10 Claims, 3 Drawing Figures

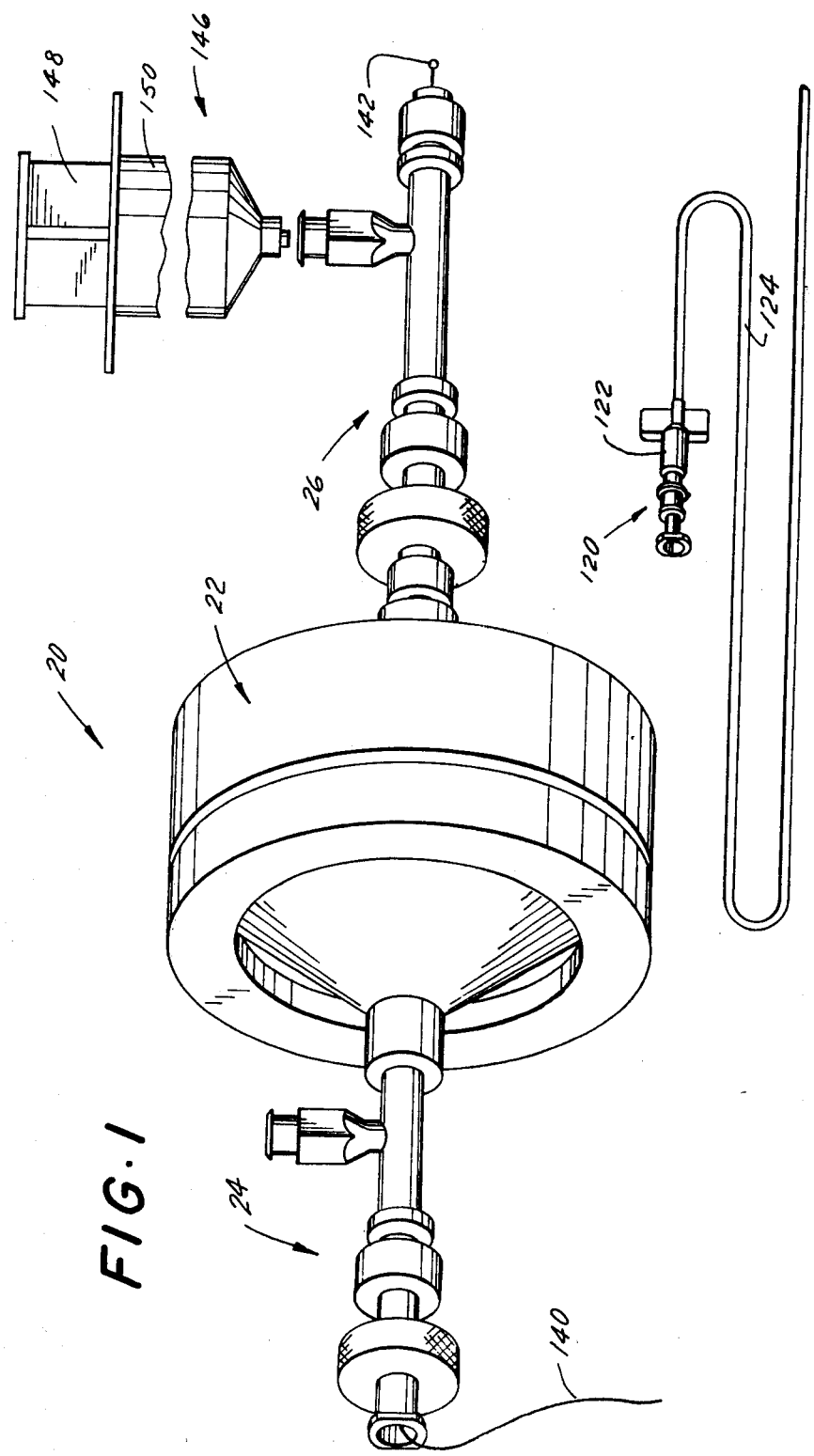

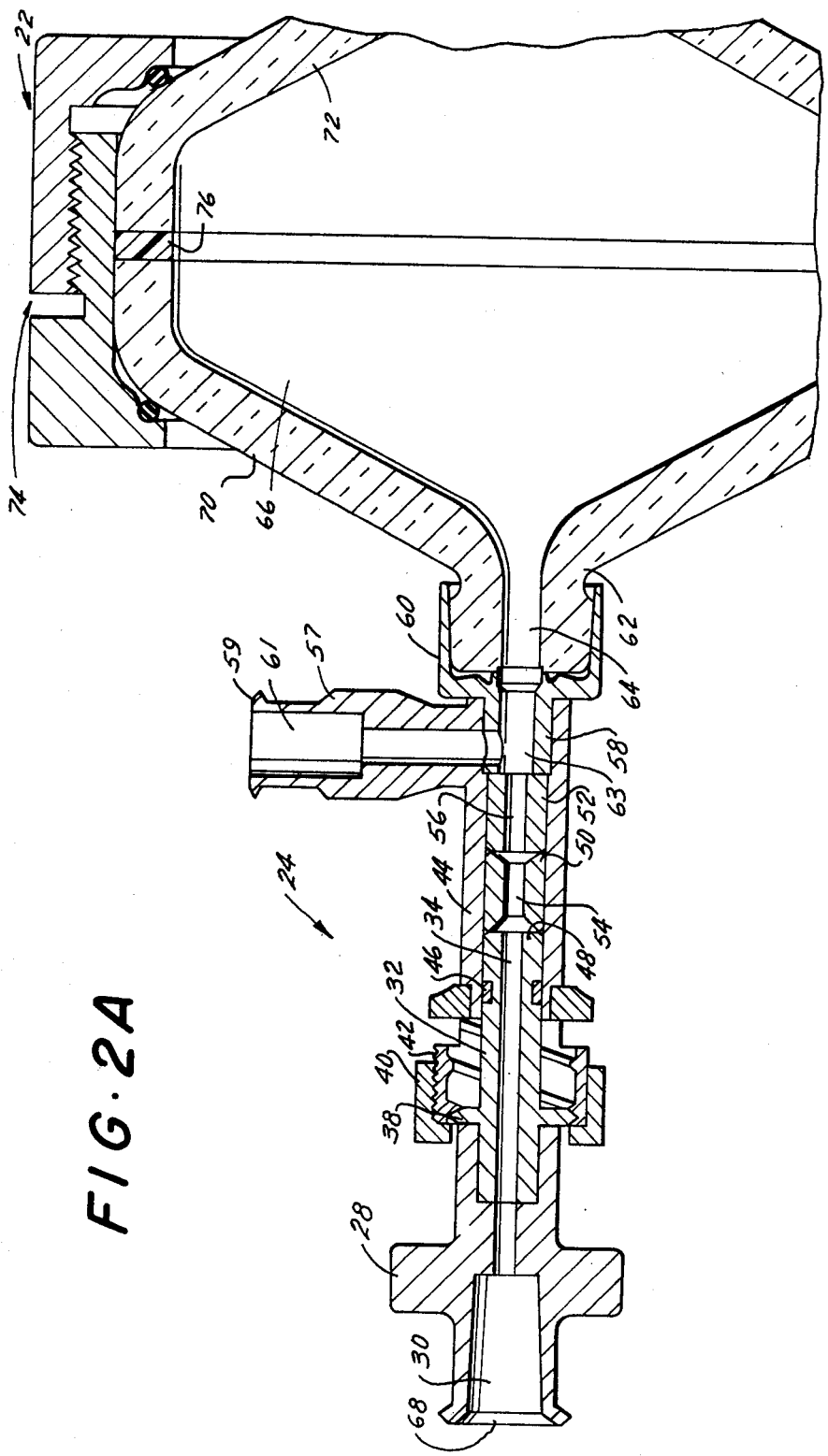

CATHETER DELIVERY SYSTEM

BACKGROUND OF THE INVENTION

In recent years various types of minute catheters have been developed for introduction into small body cavities and small vessels such as blood vessels in humans and animals. Often those minute catheters are very flexible and virtually lacking in rigidity. Furthermore, in many uses, the catheters are of great length and are extended along rather tortuous and extended paths within the body to reach desired locations.

One type of catheter which falls within this general category and criteria, is the small minature balloon catheter which has been recently developed for brain use. The catheter is threaded through tiny blood vessels in the brain into very remote locations for diagnostic and therapeutic purposes. When the catheter has reacted the desired location, it is subjected to various uses for treatment purposes including the introduction of fluids to the various sites or for expanding the minature balloons to lock the catheter at a particular location and often to occlude the minute vessel for further diagnostic and therapeutic purposes.

Naturally in order to limit the chances of injury to the patient and to allow it to be directed long distances by natural blood flow, it is desirable to have the most flexible and least rigid structure as possible for the member or catheter being introduced. This naturally presents various problems. For example once the rigidity is removed from the member, it is extremely difficult to advance the member into the vessel properly. For larger catheters, various guide wires and similar members have been utilized in the past for this purpose.

More recently, attempts have been made to replace the guide wires which can only be used on the larger catheter, due to the size required for proper functioning, with a suitable method for the minute catheters. As a replacement, various fluid delivery systems have been developed as exemplified by U.S. Pat. Nos. 3,703,174; 3,826,256; 3,911,927; and 3,982,544.

It is clear that the field of minature catheterization, particularly dealing with minute vessels in the brain is a new and fast developing medical art. Accordingly, advancement in the manner in which these catheters are handled and placed which protect the patient from trauma and possible harm are greatly desirable and needed as the techniques of the field develop.

SUMMARY OF THE INVENTION

With the above background in mind, it is among the primary objectives of the present invention to provide a method and apparatus for delivering small flexible members such as minature balloon catheters into minute body cavities such as small blood vessels in the brain.

The apparatus is simple, efficient and easy to operate and of low cost construction. It provides means for feeding the catheter to the interior of the body with minimum danger of trauma or harm to the patient and by means of a fluid delivery system of a unique design.

It is an objective to store the major portion of the member to be delivered in a chamber in coiled or loose fashion with one end extending from a forward open end of the chamber and the other end extending from the rear open end of the chamber. A first valve retains the rear end of the member in fixed position and a second valve retains the forward end of the member in a fixed position. A fluid pressure source is attached to the apparatus to direct fluid through a nozzle at the forward end and when the second valve is released the fluid will engage and entrain the forward end of the member and direct the forward end and a predetermined portion of the member from the chamber through the nozzle at the forward end of the apparatus and into a body cavity.

Introduction into the body cavity is achieved by providing a preplaced catheter at an introducing location on the body and attaching it to the forward end of the apparatus in position to receive the forward end of the member therein so that when the member is directed from the apparatus through the nozzle it will travel through the catheter to the desired location. The valve at the rear end of the apparatus retains the rear end of the member in position for interconnection with other apparatus at a later time for therapeutic, diagnostic or operational purposes.

The apparatus can be removed from the member when the member has been properly situated in the body cavity by opening the first valve and separating the chamber from the forward nozzle. The member which remains threaded through the forward nozzle can then be attached to desired equipment for further therapeutic, diagnostic or medical purposes.

The present invention is particularly adaptable for use in placing minute highly flexible and non-rigid balloon catheters in small blood vessels in the brain where the vessel must travel along a very tortuous path to a desired location. Once a balloon catheter has been introduced by entrainment of the forward portion thereof and extension into the desired position in the body cavity, the proper fluid can be introduced into the rear end of the balloon catheter to expand the balloon in the desired manner and/or therapeutic or diagnostic fluid can be introduced through the catheter and expelled through the balloon end.

A further objective of the present apparatus is to enable the retention of the member within the apparatus prior to delivery thereof into the in site catheter and enable fluid to be introduced and withdrawn through the nozzle and fluid port and accordingly through the interconnected catheter for aspiration and other purposes prior to introduction of the minature member upon release of the second valve at the forward end of the chamber.

It is also an objective of the invention to arrange the removably connected component so that the nozzle is located between the chamber and the location for introduction into the body. This permits removal of the chamber after introduction of the member to the proper location and thereby facilitates further interconnection of additional equipment for diagnostic and medical purposes. Also, removal of the chamber permits flushing independent of the presence of the delivery chamber. In fact, flushing can be accomplished independent of the chamber when it is still connected in the system due to valving structure located forward of the chamber. Thus, the chamber portion can be clamped off and flushing can occur through the nozzle forward of the chamber. In this manner, clotting can be minimized during the entire procedural operation with or without the presence of the delivery chamber. It should also be noted that by locating the delivery chamber at the rear of the interconnected apparatus, removal of the delivery chamber is facilitated if desirable. Naturally the delivery system can be retained as long as needed as part of the interconnected system.

In summary, a system is provided for delivering a small elongated flexible member into a body cavity. The apparatus includes a storage chamber open at both ends for containing substantially the entire length of the member to be delivered with one end extending through the opening at the forward end of the chamber and the other end extending through the opening at the rear end of the chamber. A first valve means is attached to the rear end of the chamber and has a passageway therethrough in communication with the interior of the chamber so that extension of the member through the valve means and closing of the valve will retain the member in fixed position. A fluid port is in position between the valve and the chamber and in communication with the interior of the chamber. Nozzle means is attached to the forward end of the chamber and has a passageway therethrough in communication with the interior of the chamber. Second valve means is on the nozzle means in position to fix the one end of the member in position when extended through the nozzle means from the chamber. Fluid pressure means is adapted to be connected to a source of fluid pressure and to direct fluid through the nozzle means so that when the second valve means is opened the one end of the member and a portion in the chamber will be delivered through the forward end of the nozzle and from the apparatus.

The system is designed so that the rear end of the member is held in fixed position while a predetermined portion of the central portion of the member and the forward end is entrained by fluid exiting through a nozzle at the location of the forward end of the member to deliver the desired portion of the member along a predetermined path into a body cavity.

With the above objectives among others in mind, reference is made to the attached drawings.

BRIEF DESCRIPTION OF THE DRAWINGS

In The Drawings:

FIG. 1 is a perspective view of the apparatus of the invention and a catheter through which the member in the apparatus is to be directed into the body cavity;

FIG. 2a is a fragmentary sectional elevational view of a portion of the apparatus of the invention;

DETAILED DESCRIPTION

Figure 2B:
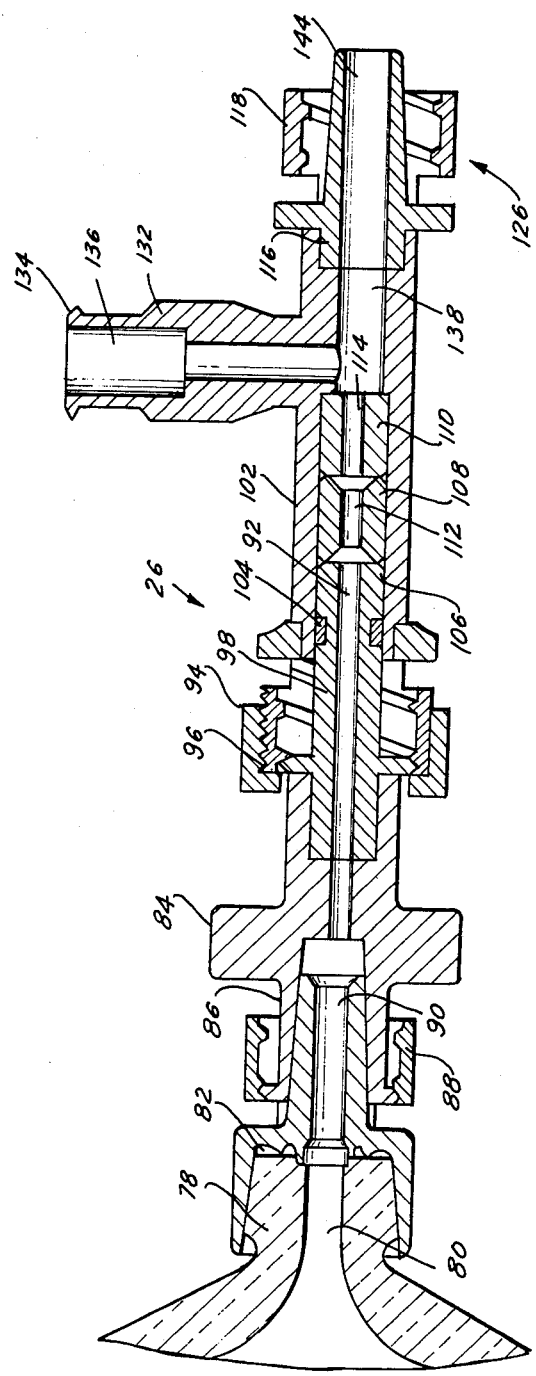
FIG. 2b is a fragmentary sectional elevational view of the remaining portion of the apparatus of the invention.

Apparatus 20 as depicted in FIG. 1 includes an enlarged cylindrical chamber 22 with a valve assembly 24 extending from the rear end of the chamber and a nozzle assembly 26 extending from the forward end thereof. A through passageway extends the entire length of apparatus 20 which is open at the forward end and open at the rear end.

Turning to FIG. 2a, at the rear end of apparatus 20, the valve assembly 24 is constructed of a number of components. A thumb screw 28 having a passageway 30 therethrough is mounted on a tubular plug 32. The plug 32 has a passageway 34 therethrough. The plug 32 has towards its rear end a rim 38. Interconnection between thumb screw 28 and plug 32 provides a communication passageway by interconnected passages 30 and 34.

The forward end of plug 32 extends within hollow tubular neck of valve member 44 and is retained in position by a retainer nut 40 threaded onto the outer surface of portion 42. The forward end of plug 32 is sealed with the inner wall of the hollow passageway of neck 44 by means of a gasket 46. The forward edge 48 of plug 32 abuts against a bushing 50 which in turn abuts against a gasket 52. Bushing 50 has a central passageway 54 therethrough which communicates with a central passageway 56 in gasket 52 to continue the passageway through valve assembly 24. The valve member 44 has its forward end mounted on the reduced diameter neck 58 of an adapter 60 which has a large diameter portion mounted in conventional fashion to a reduced diameter rear neck portion 62 of chamber 22. Neck 62 has an opening 64 therein to provide communication with the hollow interior 66 of the chamber and the remaining interconnected passage network to the rear end 68 of thumb screw 28. The members of valve assembly 24 are interconnected in a conventional manner so that rotation of thumb screw 28 between two relative positions will open and close the passage network through the valve assembly by compressing gasket 52 and accordingly open and close a flow path therethrough when a small tubular member such as a catheter is passed through the interconnecting passageway.

A side port 57 is positioned on the valve member 44 just behind the adapter 60. It has a conventional surface 59 for interconnection to a syringe or similar device for fluid injection into the passageway 61 communicating with passageway 63 in the reduced diameter neck 58 of adapter 60.

Chamber 22 is formed of two mating halves 70 and 72 shaped to form the hollow interior chamber 66. The halves are held together by means of a lock nut assembly 74 and sealed at their mating edges by a conventional washer 76.

As shown in FIG. 2B, similar to the reduced neck portion 62 at the rear end of chamber 22, a reduced neck portion 78 is at the forward end of chamber 22 and has an opening 80 therethrough to communicate with the passageway through nozzle assembly 26. Nozzle assembly 26 includes an adapter 82 similar to adapter 60 at the rear end of the chamber and it is conventional to use a well known type of luer lock adapter tip for this purpose. A thumb screw 84 similar to thumb screw 28 is mounted on the reduced diameter forward neck portion 86 of adapter 82 and a nut 88 retains these two parts together. Adapter 82 contains a passageway 90 therethrough in communication with passageway 92 through the thumb screw 84 to continue the outlet passage from opening 80 in the forward end of the chamber. A retainer nut 94 is mounted on the threaded outer surface 96 of tube 102 to retain the thumb screw 84. Thumb screw 84 is mounted on a tubular plug 98 having a passageway 92 therethrough in communication with passageway 90.

The forward end of plug 98 extends within the hollow tubular neck of valve member 102. The forward end of plug 98 is sealed with the inner wall of the passageway of neck 102 by means of a gasket 104. The forward edge 106 of plug 98 abuts against a bushing 108 which in turn abuts against a gasket 110. Bushing 108 has a passageway 112 therethrough which communicates with a passageway 114 in gasket 110 to continue the passageway through the valve assembly 26.

The members of valve assembly 26 are interconnected in a manner such that rotation of thumb screw 84 between two relative positions will open and close the passage network through the valve assembly by compressing gasket 110 and accordingly open and close a flow path therethrough when a small tubular member such as a catheter is passed through the interconnecting passageways.

An adapter assembly 126 is on the forward end of nozzle assembly 26 and includes a hollow plug 116 and surrounding threaded coupling ring 118 for interconnection in a conventional luer lock fashion with the end of a catheter assembly of the type depicted in FIG. 1.

Catheter assembly 120 in FIG. 1 includes a conventional luer lock hub arrangement 122 at its rear end and an extending hollow catheter 124 for introduction into the body in a conventional manner.

T-valve 102 includes a side port 132 which has a conventional surface 134 at its rear end for interconnection with a syringe or similar device for injection of fluid into the nozzle and a through passageway 136 communicating with the hollow interior through passageway 138 in the T-valve. In the depicted embodiment, passageway 136 is substantially perpendicular to passageway 138 in the T-valve, however, it can angularly displace to any desired degree with respect thereto as long as there is room for interconnection with the fluid source.

In operation, apparatus 20 is loaded with a minute catheter having virtually no rigidity which is designed for passage through a tortuous network in a small body vessel such as a brain blood vessel. A well known type of minature balloon catheter 140 would fall within the category of structure to be delivered by apparatus 20. As shown, balloon catheter 140 is an elongated small non-rigid member having a small balloon 142 at its forward end. It is placed in the apparatus by one of several methods. One method would be to open lock nut 74 to separate the two halves of chamber 22 in which case the majority of the elongated minature catheter 140 can be coiled or stored in loose fashion within the chamber and a forward end can then be threaded through the passageway of nozzle assembly 26 from open end 80 at the forward end of the chamber. The rear end portion of the small catheter would be threaded through open rear end 64 of the chamber and through valve assembly 24 until it extends freely from rear opening 64 of apparatus 20. As shown in FIG. 1, when properly loaded within apparatus 20, the balloon end 142 extends from open end 114 of nozzle 26 and the opposite end 140 of the member or balloon catheter extends outward from open end 68 of valve assembly 24.

Another way of loading member 140 within chamber 22 is to thread it through the assembly from either open end 68 at the rear or open end 144 at the forward end.

Thereafter, rear valve assembly 24 and the T-valve portion of nozzle 26 can be closed fixing the end portions of the member at the rear and the forward end of apparatus 20 so as to retain the member in position with the majority thereof located in the hollow interior 66 of chamber 22.

The system is then fluid filled in a conventional fashion through any of the available ports and is ready for use.

Introducing catheter 120 is then placed in the body at the desired location for delivery of the member 140 by conventional means. The luer lock hub portion 122 of the catheter is attached in a conventional manner to adapter 126 at the forward end of the nozzle. Thereafter, a syringe of a conventional nature such as syringe 146 shown in FIG. 1 is connected in a conventional manner such as by a luer lock interconnection with side port 132. The syringe plunger 148 which is reciprocally mounted in syringe barrel 150 can then be used to introduce fluid through the nozzle when pushed into the barrel and to draw fluid from the nozzle when withdrawn outwardly from the barrel. This aspiration procedure can be carried without affecting the positioning and location of member 140 mounted in the apparatus.

Thereafter, when it is desired for actual delivery of the apparatus to the location within the body, T-valve 102 is opened at the forward end of the apparatus freeing the forward end portion of member 140. Downward extension of plunger 148 to force fluid through the nozzle and out forward end 144 into the catheter 124 and accordingly into the body will cause entrainment of the forward end portion of member 140 and will move the end portion along with a majority of the member within chamber 22 through the catheter into the body cavity. Complete delivery of the entire member 140 is restricted by the means of rear valve assembly 24 holding the rear end of member 140 in fixed position.

Once delivery is completed, rear valve assembly 24 can be opened in a conventional manner and chamber 22 with valve member 24 can be removed from valve 26 in a rearward direction by unfastening luer lock 88. Therapeutic fluid introducing means or other medical devices can then be interconnected with the rear end of the minature catheter for further medical procedures. Catheter 120 and valve member 26 can also be threaded from the rear end portion of member 140, if desired, leaving only the member 140 located in the body for further medical procedures.

In this manner, the minute catheter 140 can be safely and effectively delivered in a rapid and efficient manner to a desired location within a minute blood vessel such as a human brain vessel.

It is contemplated that other fluid delivery means other than the conventional syringe 146 can be attached in a conventional manner to side port 132 to accomplish the same type of fluid delivery action.

It is contemplated that the apparatus 20 can be formed of an inexpensive low cost and even disposable material such as a plastic. The apparatus can be transparent so that the member 140 can be observed while it is located and held within the apparatus and delivered therefrom.

Thus the several aforenoted objects and advantages are most effectively attained. Although several somewhat preferred embodiments have been disclosed and described in detail herein, it should be understood that this invention is in no sense limited thereby and its scope is to be determined by that of the appended claims.

We claim:

1. Apparatus for delivering a small elongated flexible member into a body cavity comprising; a storage chamber open at both ends for containing substantially the entire length of the member to be delivered with one end extending through the opening at the forward end of the chamber and the other end extending through the opening at the rear end of the chamber, first valve means attached to the rear end of the chamber and having a passageway therethrough in communication with the interior of the chamber so that extension of the other end of the member through the valve means and closing of the valve will retain the other end of the member in fixed position, nozzle means attached to the forward end of the chamber and having a passageway therethrough in communication with the interior of said chamber, second valve means on the nozzle means and shiftable between an open position and a closed position so that when the second valve means is in the closed position it will fix the one end of the member in position when extended through the nozzle means from the chamber, and fluid pressure means adapted to be connected to a source of fluid pressure and to direct fluid through the nozzle means so that when the second valve means is in the open position the one end of the member and a portion in the chamber would be delivered through the forward end of the nozzle and from the apparatus, the fluid pressure means including a port in the nozzle means providing entrance to the fluid passageway through the nozzle, the second valve means being located between the chamber and the fluid pressure means so that when the second valve means is in the closed position the one end of the member will remain in fixed position during passage of fluid through the nozzle in either direction in response to actuation of the fluid pressure means, and the storage chamber being removably attached to the nozzle means to facilitate removal of the chamber after delivery of the member and permit use of the nozzle means independent of the storage chamber.

2. The invention in accordance with claim 1 wherein the forward end of the nozzle has means thereon for interconnection with a catheter lodged within a body cavity so that delivery of the member through the nozzle will send the member through the catheter and into the body cavity to a desired location.

3. The invention in accordance with claim 1 wherein the port in the fluid pressure means is a side port in the nozzle means providing side entrance to the fluid passageway through the nozzle, the means for interconnection to a source of fluid pressure including means for mounting a syringe in position to direct fluid through the side port and out of the forward end of the nozzle thereby producing a fluid pressure condition whereby the forward end portion and a major portion of the member is drawn from the chamber and entrained with the fluid to be ejected therewith as it leaves the forward end of the nozzle.

4. The invention in accordance with claim 1 wherein the chamber is formed with a large diameter central portion tapering in both the forward and rearward direction to a narrower diameter extending neck, the opening at the rearward and forward ends of the chamber being located at the respective rearward and forward necks of the chamber, and the major portion of the member being loosely coiled within the chamber.

5. The invention in accordance with claim 1 wherein the other end of the member extends beyond the first valve means to the exterior of the apparatus so that when the member has been positioned in the body cavity communication is provided between the other end of the one member and the one end within the body cavity, the member being hollow to permit fluid communication from the opening in the other end of the member to the interior of the body cavity.

6. The invention in accordance with claim 1 wherein the apparatus is substantially transparent to facilitate observation of the member within the apparatus.

7. The invention in accordance with claim 1 wherein the member is a very small balloon catheter substantially lacking rigidity while retaining a limited amount of flexibility and being adapted to be positioned within blood vessels.

8. A method of delivering a small elongated flexible member into a body cavity comprising; storing substantially the entire length of the member in a chamber open at both ends and with one end extending through an opening at the forward end of the chamber and the other end extending through an opening at the rear end of the chamber, releasably retaining the other end of the member in fixed position by means of a first valve attached to the rear end of the chamber, extending the one end of the member through a nozzle attached to the forward end of the chamber, providing a second releasable valve to hold the one end of the member in position until it is desired to deliver a selected portion of the member to the body cavity, directing fluid through the nozzle in a manner which will direct the selected portion of the member from the nozzle into the body cavity when the second valve is opened, the fluid being directed through the nozzle at a location whereby the fluid will entrain and thereby draw the selected portion of the member from the nozzle into the body cavity when the fluid is directed thereto, enabling fluid to be passed through the nozzle in either direction without affecting the location of the member when the second valve is closed and holding the one end of the member in position, the fluid pressure being supplied through a port in the nozzle so that as the fluid passes through the port and through the forward end of the nozzle a selected portion of the member can be entrained and drawn from the chamber and delivered through the open forward end of the nozzle when the second valve is opened and the one end of the member is released, and the chamber being removable from the nozzle and the second releasable valve without affecting the position of the member in the body cavity and the relationship between the nozzle and the second valve means and the member in the body cavity.

9. The invention in accordance with claim 8 wherein the other end of the member extends beyond the first valve means to the exterior of the apparatus so that when the member has been positioned in a body cavity communication is provided between the other end of the one member and the one end within the body cavity, the member being hollow to permit fluid communication from the opening in the other end of the member to the interior of the body cavity.

10. The invention in accordance with claim 8 wherein the member is a very small balloon catheter substantially lacking rigidity while retaining a limited amount of flexibility and being adapted to be positioned within blood vessels.

* * * * *